US008951732B2

(12) United States Patent
Pollack et al.

(10) Patent No.: US 8,951,732 B2
(45) Date of Patent: Feb. 10, 2015

(54) DROPLET-BASED NUCLEIC ACID AMPLIFICATION IN A TEMPERATURE GRADIENT

(75) Inventors: Michael G. Pollack, San Diego, CA (US); Vamsee K. Pamula, Cary, NC (US); Philip Paik, Chula Vista, CA (US); Allen Eckhardt, San Diego, CA (US)

(73) Assignee: Advanced Liquid Logic, Inc., San Diego, CA (US)

( * ) Notice: Subject to any disclaimer, the term of this patent is extended or adjusted under 35 U.S.C. 154(b) by 303 days.

(21) Appl. No.: 12/665,788

(22) PCT Filed: Jun. 23, 2008

(86) PCT No.: PCT/US2008/067879
§ 371 (c)(1),
(2), (4) Date: Dec. 21, 2009

(87) PCT Pub. No.: WO2009/002920
PCT Pub. Date: Dec. 31, 2008

(65) Prior Publication Data
US 2010/0323405 A1    Dec. 23, 2010

Related U.S. Application Data

(60) Provisional application No. 60/945,775, filed on Jun. 22, 2007.

(51) Int. Cl.
C12Q 1/68          (2006.01)
C12P 19/34         (2006.01)

(52) U.S. Cl.
CPC .................................. *C12Q 1/6846* (2013.01)
USPC ......................... 435/6.12; 435/6.1; 435/6.11

(58) Field of Classification Search
CPC ......... C12Q 1/6846; B01L 7/52; B01L 7/525; B01L 7/54
See application file for complete search history.

(56) References Cited

U.S. PATENT DOCUMENTS

| 4,636,785 A | 1/1987 | Le Pesant |
| 5,038,852 A | 8/1991 | Johnson et al. |
| 5,176,203 A | 1/1993 | Larzul |
| 5,181,016 A | 1/1993 | Lee et al. |
| 5,486,337 A | 1/1996 | Ohkawa et al. |
| 5,498,392 A | 3/1996 | Wilding et al. |
| 5,720,923 A | 2/1998 | Haff et al. |
| 5,779,977 A | 7/1998 | Haff et al. |
| 5,827,480 A | 10/1998 | Haff et al. |
| 6,033,880 A | 3/2000 | Haff et al. |
| 6,063,339 A | 5/2000 | Tisone et al. |
| 6,130,098 A | 10/2000 | Handique et al. |
| 6,180,372 B1 | 1/2001 | Franzen |
| 6,294,063 B1 | 9/2001 | Becker et al. |
| 6,337,212 B1 | 1/2002 | Nagle et al. |
| 6,565,727 B1 | 5/2003 | Shenderov |
| 6,773,566 B2 | 8/2004 | Shenderov |
| 6,790,011 B1 | 9/2004 | Le Pesant et al. |
| 6,911,132 B2 | 6/2005 | Pamula et al. |
| 6,924,792 B1 | 8/2005 | Jessop |
| 6,977,033 B2 | 12/2005 | Becker et al. |
| 6,989,234 B2 | 1/2006 | Kolar et al. |
| 7,052,244 B2 | 5/2006 | Fouillet et al. |
| 7,163,612 B2 | 1/2007 | Sterling et al. |
| 7,211,223 B2 | 5/2007 | Fouillet et al. |
| 7,255,780 B2 | 8/2007 | Shenderov |
| 7,328,979 B2 | 2/2008 | Decre et al. |
| 7,329,545 B2 | 2/2008 | Pamula et al. |
| 7,439,014 B2 | 10/2008 | Pamula et al. |
| 7,458,661 B2 | 12/2008 | Kim et al. |
| 7,531,072 B2 | 5/2009 | Roux et al. |
| 7,547,380 B2 | 6/2009 | Velev |
| 7,569,129 B2 | 8/2009 | Pamula et al. |
| 7,579,172 B2 | 8/2009 | Cho et al. |
| 7,641,779 B2 | 1/2010 | Becker et al. |
| 7,727,466 B2 | 6/2010 | Meathrel et al. |
| 7,727,723 B2 | 6/2010 | Pollack et al. |
| 7,759,132 B2 | 7/2010 | Pollack et al. |
| 7,763,471 B2 | 7/2010 | Pamula et al. |
| 7,815,871 B2 | 10/2010 | Pamula et al. |
| 7,816,121 B2 | 10/2010 | Pollack et al. |
| 7,822,510 B2 | 10/2010 | Paik et al. |
| 7,851,184 B2 | 12/2010 | Pollack et al. |
| 7,875,160 B2 | 1/2011 | Jary |
| 7,901,947 B2 | 3/2011 | Pollack et al. |

(Continued)

FOREIGN PATENT DOCUMENTS

| JP | 2006329899 A | 12/2006 |
| JP | 2006329904 A | 12/2006 |

(Continued)

OTHER PUBLICATIONS

Jie Ding, "System level architectural optimization of semi-reconfigurable microfluidic system," M.S. Thesis, Duke University Dept of Electrical Engineering, 2000.

Hyejin Moon, "Electrowetting-on-Dielectric Microfluidics: Modeling, Physics, and MALDI Application," Ph.D. Dissertation, University of California Dept. of Mechanical Engineering, published Aug. 2006.

Pollack et al., "Electrowetting-Based Actuation of Droplets for Integrated Microfluidics," Lab on a Chip (LOC), vol. 2, pp. 96-101, 2002.

Vijay Srinivasan, Vamsee K. Pamula, Richard B. Fair, "An integrated digital microfluidic lab-on-a-chip for clinical diagnostics on human physiological fluids," Lab on a Chip (LOC), vol. 4, pp. 310-315, 2004.

Fair, et al., "Integrated chemical/biochemical sample collection, pre-concentration, and analysis on a digital microfluidic lab-on-a-chip platform," Lab-on-a-Chip: Platforms, Devices, and Applications, Conf. 5591, SPIE Optics East, Philadelphia, Oct. 25-28, 2004.

Colgate E, Matsumoto H, "An Investigation of Electrowetting-based Microactuation," Journal of Vacuum Science & Technology A—Vacuume Surfaces and Films, V. 8 (4): pp. 3625-3633, Jul.-Aug. 1990.

(Continued)

*Primary Examiner* — Young J Kim
(74) *Attorney, Agent, or Firm* — William A. Barrett; Ward & Smith, P.A.

(57) ABSTRACT

A method of amplifying a nucleic acid, the method comprising cycling an amplification-ready droplet through a temperature gradient to locations within the temperature gradient suitable for effecting steps in an amplification reaction.

11 Claims, 5 Drawing Sheets

(56) References Cited

U.S. PATENT DOCUMENTS

| | | | |
|---|---|---|---|
| 7,919,330 B2 | 4/2011 | De Guzman et al. | |
| 7,922,886 B2 | 4/2011 | Fouillet et al. | |
| 7,939,021 B2 | 5/2011 | Smith et al. | |
| 7,943,030 B2 | 5/2011 | Shenderov | |
| 7,989,056 B2 | 8/2011 | Plissonnier et al. | |
| 7,998,436 B2 | 8/2011 | Pollack | |
| 8,007,739 B2 | 8/2011 | Pollack et al. | |
| 8,041,463 B2 | 10/2011 | Pollack et al. | |
| 8,048,628 B2 | 11/2011 | Pollack et al. | |
| 8,075,754 B2 | 12/2011 | Sauter-Starace et al. | |
| 8,088,578 B2 | 1/2012 | Hua et al. | |
| 8,093,062 B2 | 1/2012 | Winger et al. | |
| 8,137,917 B2 | 3/2012 | Pollack et al. | |
| 8,147,668 B2 | 4/2012 | Pollack et al. | |
| 8,202,686 B2 | 6/2012 | Pamula et al. | |
| 8,208,146 B2 | 6/2012 | Srinivasan et al. | |
| 8,221,605 B2 | 7/2012 | Pollack et al. | |
| 8,236,156 B2 | 8/2012 | Sarrut et al. | |
| 8,263,392 B2 * | 9/2012 | Gale et al. | 435/288.5 |
| 8,268,246 B2 | 9/2012 | Srinivasan et al. | |
| 8,287,711 B2 | 10/2012 | Pollack et al. | |
| 8,304,253 B2 | 11/2012 | Yi et al. | |
| 8,313,698 B2 | 11/2012 | Pollack et al. | |
| 8,317,990 B2 | 11/2012 | Pamula et al. | |
| 8,342,207 B2 | 1/2013 | Raccurt et al. | |
| 8,349,276 B2 | 1/2013 | Pamula et al. | |
| 8,388,909 B2 | 3/2013 | Pollack et al. | |
| 8,389,297 B2 | 3/2013 | Pamula et al. | |
| 8,394,249 B2 | 3/2013 | Pollack et al. | |
| 8,426,213 B2 | 4/2013 | Eckhardt et al. | |
| 8,440,392 B2 | 5/2013 | Pamula et al. | |
| 2002/0005354 A1 | 1/2002 | Spence et al. | |
| 2002/0036139 A1 | 3/2002 | Becker et al. | |
| 2002/0043463 A1 | 4/2002 | Shenderov | |
| 2002/0058332 A1 | 5/2002 | Quake et al. | |
| 2002/0081669 A1 | 6/2002 | Festock | |
| 2002/0143437 A1 | 10/2002 | Handique et al. | |
| 2003/0082081 A1 | 5/2003 | Fouillet et al. | |
| 2003/0164295 A1 | 9/2003 | Sterling | |
| 2003/0183525 A1 | 10/2003 | Elrod et al. | |
| 2003/0205632 A1 | 11/2003 | Kim et al. | |
| 2004/0031688 A1 | 2/2004 | Shenderov | |
| 2004/0055536 A1 | 3/2004 | Kolar et al. | |
| 2004/0055891 A1 | 3/2004 | Pamula et al. | |
| 2004/0058450 A1 | 3/2004 | Pamula et al. | |
| 2004/0231987 A1 | 11/2004 | Sterling et al. | |
| 2005/0106742 A1 | 5/2005 | Wahl | |
| 2005/0202489 A1 * | 9/2005 | Cho et al. | 435/6 |
| 2005/0227264 A1 | 10/2005 | Nobile et al. | |
| 2006/0021875 A1 | 2/2006 | Griffith et al. | |
| 2006/0054503 A1 | 3/2006 | Pamula et al. | |
| 2006/0164490 A1 | 7/2006 | Kim et al. | |
| 2006/0194331 A1 | 8/2006 | Pamula et al. | |
| 2006/0231398 A1 | 10/2006 | Sarrut et al. | |
| 2006/0254933 A1 | 11/2006 | Adachi et al. | |
| 2007/0023292 A1 | 2/2007 | Kim et al. | |
| 2007/0037294 A1 | 2/2007 | Pamula et al. | |
| 2007/0045117 A1 | 3/2007 | Pamula et al. | |
| 2007/0064990 A1 | 3/2007 | Roth | |
| 2007/0086927 A1 | 4/2007 | Natarajan et al. | |
| 2007/0207513 A1 | 9/2007 | Sorensen et al. | |
| 2007/0217956 A1 | 9/2007 | Pamula et al. | |
| 2007/0241068 A1 | 10/2007 | Pamula et al. | |
| 2007/0242105 A1 | 10/2007 | Srinivasan et al. | |
| 2007/0242111 A1 | 10/2007 | Pamula et al. | |
| 2007/0243634 A1 | 10/2007 | Pamula et al. | |
| 2007/0267294 A1 | 11/2007 | Shenderov | |
| 2007/0275415 A1 | 11/2007 | Srinivasan et al. | |
| 2008/0006535 A1 | 1/2008 | Paik et al. | |
| 2008/0038810 A1 | 2/2008 | Pollack et al. | |
| 2008/0044893 A1 | 2/2008 | Pollack et al. | |
| 2008/0044914 A1 | 2/2008 | Pamula et al. | |
| 2008/0050834 A1 | 2/2008 | Pamula et al. | |
| 2008/0053205 A1 | 3/2008 | Pollack et al. | |
| 2008/0105549 A1 | 5/2008 | Pamela et al. | |
| 2008/0124252 A1 | 5/2008 | Marchand et al. | |
| 2008/0142376 A1 | 6/2008 | Fouillet et al. | |
| 2008/0151240 A1 | 6/2008 | Roth | |
| 2008/0166793 A1 | 7/2008 | Beer et al. | |
| 2008/0210558 A1 | 9/2008 | Sauter-Starace et al. | |
| 2008/0247920 A1 | 10/2008 | Pollack et al. | |
| 2008/0264797 A1 | 10/2008 | Pamula et al. | |
| 2008/0274513 A1 | 11/2008 | Shenderov et al. | |
| 2008/0281471 A1 | 11/2008 | Smith et al. | |
| 2008/0283414 A1 | 11/2008 | Monroe et al. | |
| 2008/0302431 A1 | 12/2008 | Marchand et al. | |
| 2008/0305481 A1 | 12/2008 | Whitman et al. | |
| 2009/0014394 A1 | 1/2009 | Yi et al. | |
| 2009/0042319 A1 | 2/2009 | De Guzman et al. | |
| 2009/0053726 A1 | 2/2009 | Owen et al. | |
| 2009/0127123 A1 | 5/2009 | Raccurt et al. | |
| 2009/0134027 A1 | 5/2009 | Jary | |
| 2009/0142564 A1 | 6/2009 | Plissonnier et al. | |
| 2009/0155902 A1 | 6/2009 | Pollack et al. | |
| 2009/0192044 A1 | 7/2009 | Fouillet | |
| 2009/0260988 A1 | 10/2009 | Pamula et al. | |
| 2009/0263834 A1 | 10/2009 | Sista et al. | |
| 2009/0280251 A1 | 11/2009 | De Guzman et al. | |
| 2009/0280475 A1 | 11/2009 | Pollack et al. | |
| 2009/0280476 A1 | 11/2009 | Srinivasan et al. | |
| 2009/0288710 A1 | 11/2009 | Viovy et al. | |
| 2009/0291433 A1 * | 11/2009 | Pollack et al. | 435/6 |
| 2009/0304944 A1 | 12/2009 | Sudarsan et al. | |
| 2009/0321262 A1 | 12/2009 | Adachi et al. | |
| 2010/0025242 A1 | 2/2010 | Pamula et al. | |
| 2010/0025250 A1 | 2/2010 | Pamula et al. | |
| 2010/0028920 A1 | 2/2010 | Eckhardt | |
| 2010/0032293 A1 | 2/2010 | Pollack et al. | |
| 2010/0041086 A1 | 2/2010 | Pamula et al. | |
| 2010/0048410 A1 | 2/2010 | Shenderov et al. | |
| 2010/0062508 A1 | 3/2010 | Pamula et al. | |
| 2010/0068764 A1 | 3/2010 | Sista et al. | |
| 2010/0087012 A1 | 4/2010 | Shenderov et al. | |
| 2010/0096266 A1 | 4/2010 | Kim et al. | |
| 2010/0116640 A1 | 5/2010 | Pamula et al. | |
| 2010/0118307 A1 | 5/2010 | Srinivasan et al. | |
| 2010/0130369 A1 | 5/2010 | Shenderov et al. | |
| 2010/0140093 A1 | 6/2010 | Pamula et al. | |
| 2010/0143963 A1 | 6/2010 | Pollack | |
| 2010/0151439 A1 | 6/2010 | Pamula et al. | |
| 2010/0194408 A1 | 8/2010 | Sturmer et al. | |
| 2010/0258441 A1 | 10/2010 | Sista et al. | |
| 2010/0279374 A1 | 11/2010 | Sista et al. | |
| 2010/0323405 A1 | 12/2010 | Pollack et al. | |
| 2011/0100823 A1 | 5/2011 | Pollack et al. | |
| 2011/0114490 A1 | 5/2011 | Pamula et al. | |
| 2011/0118132 A1 | 5/2011 | Winger et al. | |
| 2011/0180571 A1 | 7/2011 | Srinivasan et al. | |
| 2011/0186433 A1 | 8/2011 | Pollack et al. | |
| 2011/0203930 A1 | 8/2011 | Pamula et al. | |
| 2011/0209998 A1 | 9/2011 | Shenderov | |
| 2012/0018306 A1 | 1/2012 | Srinivasan et al. | |
| 2012/0132528 A1 | 5/2012 | Shenderov et al. | |
| 2012/0165238 A1 | 6/2012 | Pamula et al. | |

FOREIGN PATENT DOCUMENTS

| | | | |
|---|---|---|---|
| WO | 0069565 A1 | 11/2000 | |
| WO | 0073655 A1 | 12/2000 | |
| WO | 2005047696 A1 | 5/2002 | |
| WO | 2004029585 A1 | 4/2004 | |
| WO | 2004030820 | 4/2004 | |
| WO | WO2004073863 A2 | 9/2004 | |
| WO | 2006013303 A1 | 2/2006 | |
| WO | 2006070162 A1 | 7/2006 | |
| WO | 2006081558 | 8/2006 | |
| WO | 2006124458 A2 | 11/2006 | |
| WO | 2006127451 A2 | 11/2006 | |
| WO | WO 2006124458 A2 * | 11/2006 | |
| WO | 2006134307 A1 | 12/2006 | |
| WO | 2006138543 | 12/2006 | |
| WO | 2007003720 A1 | 1/2007 | |
| WO | 2007012638 A1 | 2/2007 | |
| WO | 2007033990 A1 | 3/2007 | |

(56) References Cited

FOREIGN PATENT DOCUMENTS

| WO | 2007048111 | | 4/2007 |
|---|---|---|---|
| WO | 2007120240 | A2 | 10/2007 |
| WO | 2007120241 | A2 | 10/2007 |
| WO | 2007123908 | A2 | 11/2007 |
| WO | 2008051310 | A2 | 5/2008 |
| WO | 2008055256 | A3 | 5/2008 |
| WO | 2008091848 | A2 | 7/2008 |
| WO | 2008098236 | A2 | 8/2008 |
| WO | 2008101194 | A2 | 8/2008 |
| WO | 2008106678 | A1 | 9/2008 |
| WO | 2008109664 | A1 | 9/2008 |
| WO | 2008112856 | A1 | 9/2008 |
| WO | 2008116209 | A1 | 9/2008 |
| WO | 2008116221 | A1 | 9/2008 |
| WO | 2008118831 | A2 | 10/2008 |
| WO | 2008124846 | A2 | 10/2008 |
| WO | 2008131420 | A2 | 10/2008 |
| WO | 2008134153 | A1 | 11/2008 |
| WO | 2009002920 | A1 | 12/2008 |
| WO | 2009011952 | A1 | 1/2009 |

OTHER PUBLICATIONS

Vinet, F., et al., "Microarrays and microfluidic devices; miniaturized systems for biological analysis," Microelectronic Engineering 61-62 (2002) 41-47.
Chakrabarty, "Automated Design of Microfluidics-Based Biochips: connecting Biochemistry of Electronics CAD", IEEE International Conference on Computer Design, San Jose, CA, Oct. 1-4, 2006, 93-100.
Chakrabarty et al., "Design Automation Challenges for Microfluidics-Based Biochips", DTIP of MEMS & MOEMS, Montreux, Switzerland, Jun. 1-3, 2005.
Chakrabarty et al., "Design Automation for Microfluidics-Based Biochips", ACM Journal on Engineering Technologies in Computing Systems , 1(3), Oct. 2005, 186-223.
Chakrabarty, "Design, Testing, and Applications of Digital Microfluidics-Based Biochips", Proceedings of the 18th International Conf. on VLSI held jointly with 4th International Conf. on Embedded Systems Design (VLSID'05), IEEE, Jan. 3-7, 2005.
Chen et al., "Development of Mesoscale Actuator Device with Micro Interlocking Mechanism", J. Intelligent Material Systems and Structures, vol. 9, No. 4, Jun. 1998, pp. 449-457.
Chen et al., "Mesoscale Actuator Device with Micro Interlocking Mechanism", Proc. IEEE Micro Electro Mechanical Systems Workshop, Heidelberg, Germany, Jan. 1998, pp. 384-389.
Chen et al., "Mesoscale Actuator Device: Micro Interlocking Mechanism to Transfer Macro Load", Sensors and Actuators, vol. 73, Issues 1-2, Mar. 1999, pp. 30-36.
Dewey, "Towards a Visual Modeling Approach to Designing Microelectromechanical System Transducers", Journal of Micromechanics and Microengineering, vol. 9, Dec. 1999, 332-340.
Dewey et al., "Visual modeling and design of microelectromechanical system tansducers", Microelectronics Journal, vol. 32, Apr. 2001, 373-381.
Fair et al., "A Micro- Watt Metal-Insulator-Solution-Transport (MIST) Device for Scalable Digital Bio-Microfluidic Systems", IEEE IEDM Technical Digest, 2001, 16.4.1-4.
Fair et al., "Advances in droplet-based bio lab-on-a-chip", BioChips 2003, Boston, 2003.
Fair et al., "Bead-Based and Solution-Based Assays Performed on a Digital Microfluidic Platform", Biomedical Engineering Society (BMES) Fall Meeting, Baltimore, MD, Oct. 1, 2005.
Fair, "Biomedical Applications of Electrowetting Systems", 5th International Electrowetting Workshop, Rochester, NY, May 31, 2006.
Fair et al., "Chemical and Biological Applications of Digital-Microfluidic Devices", IEEE Design & Test of Computers, vol. 24(1), Jan.-Feb. 2007, 10-24.
Fair et al., "Chemical and biological pathogen detection in a digital microfluidic platform", DARPA Workshop on Microfluidic Analyzers for DoD and National Security Applications, Keystone, CO, 2006.
Fair, "Digital microfluidics: is a true lab-on-a-chip possible?", Microfluid Nanofluid, vol. 3, Mar. 8, 2007, 245-281.
Fair, "Droplet-based microfluidic Genome sequencing", NHGRI PI's meeting, Boston, 2005.
Fair et al., "Electrowetting-based On-Chip Sample Processing for Integrated Microfluidics", IEEE Inter. Electron Devices Meeting (IEDM), 2003, 32.5.1-32.5.4.
Fouillet et al., "Design and Validation of a Complex Generic Fluidic Microprocessor Based on EWOD Droplet for Biological Applications", 9th International Conference on Miniaturized Systems for Chem and Life Sciences, Boston, MA, Oct. 9-13, 2005, 58-60.
Jun et al., "Valveless Pumping using Traversing Vapor Bubbles in Microchannels", J. Applied Physics, vol. 83, No. 11, Jun. 1998, pp. 5658-5664.
Kim et al., "MEMS Devices Based on the Use of Surface Tension", Proc. Int. Semiconductor Device Research Symposium (ISDRS'99), Charlottesville, VA, Dec. 1999, pp. 481-484.
Kim, "Microelectromechanical Systems (MEMS) at the UCLA Micromanufacturing Lab", Dig. Papers, Int. Microprocesses and Nanotechnology Conf. (MNC'98), Kyungju, Korea, Jul. 1998, pp. 54-55.
Kim et al., "Micromachines Driven by Surface Tension", AIAA 99-3800, 30th AIAA Fluid Dynamics Conference, Norfolk, VA, (Invited lecture), Jun. 1999, pp. 1-6.
Lee et al., "Microactuation by Continuous Electrowetting Phenomenon and Silicon Deep Rie Process", Proc. MEMS (DSC—vol. 66) ASME Int. Mechanical Engineering Congress and Exposition, Anaheim, CA, Nov. 1998, 475-480.
Lee et al., "Liquid Micromotor Driven by Continuous Electrowetting", Proc. IEEE Micro Electro Mechanical Systems Workshop, Heidelberg, Germany, Jan. 1998, pp. 538-543.
Lee et al., "Theory and Modeling of Continuous Electrowetting Microactuation", Proc. MEMS (MEMS-vol. 1), ASME Int. Mechanical Engineering Congress and Exposition, Nashville, TN, Nov. 1999, pp. 397-403.
Paik et al., "Adaptive Cooling of Integrated Circuits Using Digital Microfluidics", accepted for publication in IEEE Transactions on VLSI Systems, 2007, and Artech House, Norwood, MA, 2007.
Paik, "Adaptive Hot-Spot Cooling of Integrated Circuits Using Digital Microfluidics", Dissertation, Dept. of Electrical and Computer Engineering, Duke University, Apr. 25, 2006, 1-188.
Paik et al., "Adaptive hot-spot cooling of integrated circuits using digital microfluidics", Proceedings ASME International Mechanical Engineering Congress and Exposition, Orlando, Florida, USA. IMECE2005-81081, Nov. 5-11, 2005, 1-6.
Paik et al., "Coplanar Digital Microfluidics Using Standard Printed Circuit Board Processes", 9th International Conference on Miniaturized Systems for Chemistry and Life Sciences (MicroTAS), Boston, MA; Poster, 2005.
Paik et al., "Coplanar Digital Microfluidics Using Standard Printed Circuit Board Processes", 9th Int'l Conf. on Miniaturized Systems for Chemistry and Life Sciences, Boston, MA, Oct. 9-13, 2005, 566-68.
Paik et al., "Droplet-Based Hot Spot Cooling Using Topless Digital Microfluidics on a Printed Circuit Board", Int'l Workshops on Thermal Investigations of ICs and Systems (THERMINIC), 2005, 278-83.
Paik et al., "Electrowetting-based droplet mixers for microfluidic systems", Lab on a Chip (LOC), vol. 3. (more mixing videos available, along with the article, at LOC's website), 2003, 28-33.
Paik et al., "Programmable flow-through real-time PCR using digital microfluidics", Proc. Micro Total Analysis Systems (µTAS), Handout, 2007.
Paik et al., "Programmable flow-through real-time PCR using digital microfluidics", Proc. Micro Total Analysis Systems (µTAS), Poster, 2007.
Paik et al., "Rapid Droplet Mixers for Digital Microfluidic Systems", Masters Thesis, Duke Graduate School., 2002, 1-82.
Paik et al., "Rapid droplet mixers for digital microfluidic systems", Lab on a Chip, vol. 3.(More mixing videos available, along with the article, at LOC's website.), 2003, 253-259.
Paik et al., "Thermal effects on Droplet Transport in Digital Microfluids with Application to Chip Cooling Processing for Inte- (56) References Cited

OTHER PUBLICATIONS grated Microfluidics", International Conference on Thermal, Mechanics, and Thermomechanical Phenomena in Electronic Systems (ITherm), 2004, 649-654.
Pamula, "A digital microfluidic platform for multiplexed explosive detection", Chapter 18, Electronics Noses and Sensors for the Detection of Explosives, Eds., J.W. Gardner and J. Yinon, Kluwer Academic Publishers, 2004.
Pamula et al., "A droplet-based lab-on-a-chip for colorimetric detection of nitroaromatic explosives", Proceedings of Micro Electro Mechanical Systems, 2005, 722-725.
Pamula et al., "Cooling of integrated circuits using droplet-based microfluidics", Proc. ACM Great Lakes Symposium on VLSI, Apr. 2003, 84-87.
Pamula et al., "Digital microfluidic lab-on-a-chip for protein crystallization", 5th Protein Structure Initiative "Bottlenecks" Workshop, NIH, Bethesda, MD, Apr. 13-14, 2006,1-16.
Pamula et al., "Digital Microfluidics Platform for Lab-on-a-chip applications", Duke University Annual Post Doctoral Research Day, 2002.
Pamula et al., "Microfluidic electrowetting-based droplet mixing", IEEE, 2002, 8-10.
Pamula et al. (CO-CHAIR, "Digital Microfluidics for Lab-on-a-Chip Applications", "Emerging CAD Challenges for Biochip Design" Workshop, Conference on Design, Automation, and Test in Europe (DATE), Munich, Germany, Advance Programme, 2006, pp. 85-87.
Pollack et al., "Electrowetting-based actuation of liquid droplets for microfluidic applications", Appl. Phys. Letters, vol. 77, No. 11, Sep. 11, 2000, 1725-1726.
Pollack, "Electrowetting-based Microactuation of Droplets for Digital Microfluidics", PhD Thesis, Department of Electrical and Computer Engineering, Duke University, 2001.
Pollack et al., "Electrowetting-Based Microfluidics for High-Throughput Screening", smallTalk 2001 Conference Program Abstract, San Diego, Aug. 27-31, 2001, 149.
Pollack et al., "Investigation of electrowetting-based microfluidics for real-time PCR applications", Proc. 7th Int'l Conference on Micro Total Analysis Systems (mTAS), Squaw Valley, CA, Oct. 5-9, 2003, 619-622.
Ren et al., "Automated electrowetting-based droplet dispensing with good reproducibility", Proc. Micro Total Analysis Systems (mTAS), 7th Int. Conf.on Miniaturized Chem and Biochem Analysis Systems, Squaw Valley, CA, Oct. 5-9, 2003, 993-996.
Ren et al., "Automated on-chip droplet dispensing with volume control by electro-wetting actuation and capacitance metering", Sensors and Actuators B: Chemical, vol. 98, Mar. 2004, 319-327.
Ren et al., "Design and testing of an interpolating mixing architecture for electrowetting-based droplet-on-chip chemical dilution", Transducers, 12th International Conference on Solid-State Sensors, Actuators and Microsystems, 2003, 619-622.
Ren et al., "Dynamics of electro-wetting droplet transport", Sensors and Actuators B (Chemical), vol. B87, No. 1, Nov. 15, 2002, 201-206.
Ren et al., "Micro/Nano Liter Droplet Formation and Dispensing by Capacitance Metering and Electrowetting Actuation", IEEE-NANO, 2002, 369-372.
Sherman et al., "Flow Control by Using High-Aspect-Ratio, In-Plane Microactuators", Sensors and Actuators, vol. 73, 1999, pp. 169-175.
Sherman et al., "In-Plane Microactuator for Fluid Control Application", Proc. IEEE Micro Electro Mechanical Systems Workshop, Heidelberg, Germany, Jan. 1998, pp. 454-459.
Sista, "Development of a Digital Microfluidic Lab-on-a-Chip for Automated Immunoassays with Magnetically Responsive Beads", PhD Thesis, Department of Chemical Engineering, Florida State University, 2007.
Srinivasan et al., "3-D imaging of moving droplets for microfluidics using optical coherence tomography", Proc. 7th International Conference on Micro Total Analysis Systems (mTAS), Squaw Valley, CA, Oct. 5-9, 2003, 1303-1306.
Srinivasan et al., "A digital microfluidic biosensor for multianalyte detection", Proc. IEEE 16th Annual Int'l Conf. on Micro Electro Mechanical Systems Conference, 2003, 327-330.
Srinivasan, "A Digital Microfluidic Lab-on-a-Chip for Clinical Diagnostic Applications", Ph.D. thesis, Dept of Electrical and Computer Engineering, Duke University, 2005.
Srinivasan et al., "Clinical diagnostics on human whole blood, plasma, serum, urine, saliva, sweat and tears on a digital microfluidic platform", Proc. 7th International Conference on Micro Total Analysis Systems (mTAS), Squaw Valley, CA, Oct. 5-9, 2003, 1287-1290.
Srinivasan et al., "Droplet-based microfluidic lab-on-a-chip for glucose detection", Analytica Chimica Acta, vol. 507, No. 1, 2004, 145-150.
Srinivasan et al., "Protein Stamping for MALDI Mass Spectrometry Using an Electrowetting-based Microfluidic Platform", Lab-on-a-Chip: Platforms, Devices, and Applications, Conf. 5591, SPIE Optics East, Philadelphia, Oct. 25-28, 2004.
Srinivasan et al., "Scalable Macromodels for Microelectromechanical Systems", Technical Proc. 2001 Int. Conf. on Modeling and Simulation of Microsystems, 2001, 72-75.
Su et al., "Yield Enhancement of Digital Microfluidics-Based Biochips Using Space Redundancy and Local Reconfiguration", Proc. Design, Automation and Test in Europe (DATE) Conf., IEEE, 2005, 1196-1201.
Sudarsan et al., "Printed circuit technology for fabrication of plastic based microfluidic devices", Analytical Chemistry vol. 76, No. 11, Jun. 1, 2004, Previously published on-line, May 2004, 3229-3235.
Wang et al., "Droplet-based micro oscillating-flow PCR chip", J. Micromechanics and Microengineering, vol. 15, 2005, 1369-1377.
Wang et al., "Efficient in-droplet separation of magnetic particles for digital microfluidics", Journal of Micromechanics and Microengineering, vol. 17, 2007, 2148-2156
Xu et al., "A Cross-Referencing-Based Droplet Manipulation Method for High-Throughput and Pin-Constrained Digital Microfluidic Arrays", Proceedings of conference on Design, Automation and Test in Europe, Apr. 2007
Xu et al., "Automated Design of Pin-Constrained Digital Microfluidic Biochips Under Droplet-Interference Constraints", ACM Journal on Emerging Technologies is Computing Systems, vol. 3(3), 2007, 14:1-14:23.
Xu et al., "Defect-Aware Synthesis of Droplet-Based Microfluidic Biochips", IEEE, 20th International Conference on VLSI Design, 2007.
Xu et al., "Droplet-Trace-Based Array Partitioning and a Pin Assignment Algorithm for the Automated Design of Digital Microfluidic Biochips", Codes, 2006, 112-117.
Xu et al., "Integrated Droplet Routing in the Synthesis of Microfluidic Biochips", IEEE, 2007, 948-953.
Xu et al., "Parallel Scan-Like Test and Multiple-Defect Diagnosis for Digital Microfluidic Biochips", IEEE Transactions on Biomedical Circuits and Systems, vol. 1(2), Jun. 2007, 148-158.
Xu et al., "Parallel Scan-Like Testing and Fault Diagnosis Techniques for Digital Microfluidic Biochips", Proceedings of the 12th IEEE European Test Symposium (ETS), Freiburg, Germany, May 20-24, 2007, 63-68.
Yao et al., "Spot Cooling Using Thermoelectric Microcooler", Proc. 18th Int. Thermoelectric Conf, Baltimore, VA, pp. 256-259, Aug. 1999
Yi et al., "Channel-to-droplet extractions for on-chip sample preparation", Solid-State Sensor, Actuators and Microsystems Workshop (Hilton Head '06), Hilton Head Island, SC, Jun. 2006, 128-131.
Yi et al., "Characterization of electrowetting actuation on addressable single-side coplanar electrodes", Journal of Micromechanics and Microengineering, vol. 16., Oct. 2006, 2053-2059.
Yi et al., "EWOD Actuation with Electrode-Free Cover Plate", Digest of Tech. papers, 13th International Conference on Solid-State Sensors, Actuators and Microsystems (Transducers '05), Seoul, Korea, Jun. 5-9, 2005, 89-92.
Yi et al., "Geometric surface modification of nozzles for complete transfer of liquid drops", Solid-State Sensor, Actuator and Microsystems Workshop, Hilton Head Island, South Carolina, Jun. 6-10, 2004, 164-167.

(56) References Cited

OTHER PUBLICATIONS

Yi, "Soft Printing of Biological Liquids for Micro-arrays: Concept, Principle, Fabrication, and Demonstration", Ph.D. dissertation, UCLA, 2004.

Yi et al., "Soft Printing of Droplets Digitized by Electrowetting", Transducers 12th Int'l Conf. on Solid State Sensors, Actuators and Microsystems, Boston, Jun. 8-12, 2003, 1804-1807.

Yi et al., "Soft Printing of Droplets Pre-Metered by Electrowetting", Sensors and Actuators A: Physical, vol. 114, Jan. 2004, 347-354.

Zeng et al., "Actuation and Control of Droplets by Using Electrowetting-on-Dielectric", Chin. Phys. Lett., vol. 21(9), 2004, 1851-1854.

Zhao et al., "In-droplet particle separation by travelling wave dielectrophoresis (twDEP) and EWOD", Solid-State Sensor, Actuators and Microsystems Workshop (Hilton Head.'06), Hilton Head Island, SC, Jun. 2006, 181-184.

Zhao et al., "Micro air bubble manipulation by electrowetting on dielectric (EWOD): transporting, splitting, merging and eliminating of bubbles", Lab on a chip, vol. 7, 2007, First published as an Advance Article on the web, Dec. 4, 2006, 273-280.

PCT International Search Report and Written Opinion for PCT/US2008/067879 dated Oct. 8, 2008.

* cited by examiner

DROPLET-BASED NUCLEIC ACID AMPLIFICATION IN A TEMPERATURE GRADIENT

1 GOVERNMENT INTEREST

This invention was made with government support under AI066590-02, awarded by the National Institutes of Health of the United States. The United States Government has certain rights in the invention.

2 BACKGROUND

Compared to stationary formats, "flow-through" polymerase chain reaction (PCR) offers advantages in terms of speed, sample throughput, ease of thermal control and integration with other microfluidic operations. However, current flow-through PCR approaches that are based on continuous flow of reactants in fixed channels lack flexibility because the available thermal profiles are determined by the physical layout of the channels. There is a need for droplet-based approaches to flow-through PCR.

3 SUMMARY OF THE INVENTION

The invention provides a method of amplifying a nucleic acid. The method involves cycling an amplification-ready droplet through a temperature gradient to locations within the temperature gradient suitable for effecting steps in an amplification reaction. The cycling may be accomplished using droplet operations on a droplet operations surface mediated by electrodes associated with the surface. The droplet is shuttled through an oil-based filler fluid on a droplet actuator to the locations.

The locations may include locations having temperatures suitable for: (a) adjusting the droplet to a temperature selected to denature double stranded nucleic acid in the droplet into single-stranded DNA (typically about 90-100° C.); and (b) adjusting the droplet temperature selected to permit primers to anneal to their complementary sequences on the nucleic acid template strands (typically about 50-75° C.); and (c) adjusting the droplet temperature selected to facilitate extension of the double stranded segment of the nucleic acid to be extended by incorporation of additional nucleotides (typically about 70-75° C.).

In some cases, the droplet is shuttled or transported to different locations within the temperature gradient to identify improved amplification patterns based on the results of varying the locations. For example, the method may be used to independently varying anneal, extension and/or denaturation location within the thermal gradient to identify an improved anneal location or temperature. The method may further involve executing an improved PCR amplification protocol using the newly identified locations. In some cases, the improvement may involve minimizing denaturation and annealing/extension times to achieve minimum analysis time.

The temperature gradient may, for example, be established using a heating element arranged to heat filler fluid at a locus of an electrode path. In other cases, the temperature gradient is established (a) using a heating element arranged to heat filler fluid at a first locus of an electrode array or path; and (b) a heat sink element arranged to heat filler fluid at a second locus of an electrode array or path. Any number of heating elements and/or heat sinks may be used.

In some cases, the method also involves mapping the temperature gradient of the droplet actuator. Further, the mapped temperature gradient may be associated with droplet operations electrodes at specific temperatures in order to select locations within the gradient for conducting the various amplification steps.

4 DEFINITIONS

As used herein, the following terms have the meanings indicated.

"Activate" with reference to one or more electrodes means effecting a change in the electrical state of the one or more electrodes which results in a droplet operation.

"Droplet" means a volume of liquid on a droplet actuator that is at least partially bounded by filler fluid. For example, a droplet may be completely surrounded by filler fluid or may be bounded by filler fluid and one or more surfaces of the droplet actuator. Droplets may take a wide variety of shapes; nonlimiting examples include generally disc shaped, slug shaped, truncated sphere, ellipsoid, spherical, partially compressed sphere, hemispherical, ovoid, cylindrical, and various shapes formed during droplet operations, such as merging or splitting or formed as a result of contact of such shapes with one or more surfaces of a droplet actuator.

"Droplet operation" means any manipulation of a droplet on a droplet actuator. A droplet operation may, for example, include: loading a droplet into the droplet actuator; dispensing one or more droplets from a source droplet; splitting, separating or dividing a droplet into two or more droplets; transporting a droplet from one location to another in any direction; merging or combining two or more droplets into a single droplet; diluting a droplet; mixing a droplet; agitating a droplet; deforming a droplet; retaining a droplet in position; incubating a droplet; heating a droplet; vaporizing a droplet; cooling a droplet; disposing of a droplet; transporting a droplet out of a droplet actuator; other droplet operations described herein; and/or any combination of the foregoing. The terms "merge," "merging," "combine," "combining" and the like are used to describe the creation of one droplet from two or more droplets. It should be understood that when such a term is used in reference to two or more droplets, any combination of droplet operations that are sufficient to result in the combination of the two or more droplets into one droplet may be used. For example, "merging droplet A with droplet B," can be achieved by transporting droplet A into contact with a stationary droplet B, transporting droplet B into contact with a stationary droplet A, or transporting droplets A and B into contact with each other. The terms "splitting," "separating" and "dividing" are not intended to imply any particular outcome with respect to size of the resulting droplets (i.e., the size of the resulting droplets can be the same or different) or number of resulting droplets (the number of resulting droplets may be 2, 3, 4, 5 or more). The term "mixing" refers to droplet operations which result in more homogenous distribution of one or more components within a droplet. Examples of "loading" droplet operations include microdialysis loading, pressure assisted loading, robotic loading, passive loading, and pipette loading. Droplet operations may be electrode-mediated. In some cases, droplet operations are further facilitated by the use of hydrophilic and/or hydrophobic regions on surfaces and/or by physical obstacles.

The terms "top" and "bottom," when used, e.g., to refer to the top and bottom substrates of the droplet actuator, are used for convenience only; the droplet actuator is functional regardless of its position in space.

When a given component, such as a layer, region or substrate, is referred to herein as being disposed or formed "on" another component, that given component can be directly on the other component or, alternatively, intervening components (for example, one or more coatings, layers, interlayers, electrodes or contacts) can also be present. It will be further understood that the terms "disposed on" and "formed on" are used interchangeably to describe how a given component is positioned or situated in relation to another component. Hence, the terms "disposed on" and "formed on" are not intended to introduce any limitations relating to particular methods of material transport, deposition, or fabrication.

When a liquid in any form (e.g., a droplet or a continuous body, whether moving or stationary) is described as being "on", "at", or "over" an electrode, array, matrix or surface, such liquid could be either in direct contact with the electrode/array/matrix/surface, or could be in contact with one or more layers or films that are interposed between the liquid and the electrode/array/matrix/surface.

When a droplet is described as being "on" or "loaded on" a droplet actuator, it should be understood that the droplet is arranged on the droplet actuator in a manner which facilitates using the droplet actuator to conduct droplet operations on the droplet, the droplet is arranged on the droplet actuator in a manner which facilitates sensing of a property of or a signal from the droplet, and/or the droplet has been subjected to a droplet operation on the droplet actuator, e.g., a layer of filler fluid.

5 DESCRIPTION

Digital microfluidic systems that are based on the electrowetting effect allow individual droplets to be rapidly and programmably transported between discrete positions on a surface using an array of electrodes. The invention provides a PCR chip assembly that has a thermal gradient that is generated across the surface of an electrode array. The thermal gradient permits thermal cycling to be performed by transporting individual droplets between different positions within the thermal gradient. Other Embodiments of the invention will be apparent from the ensuing discussion.

Figure 1:
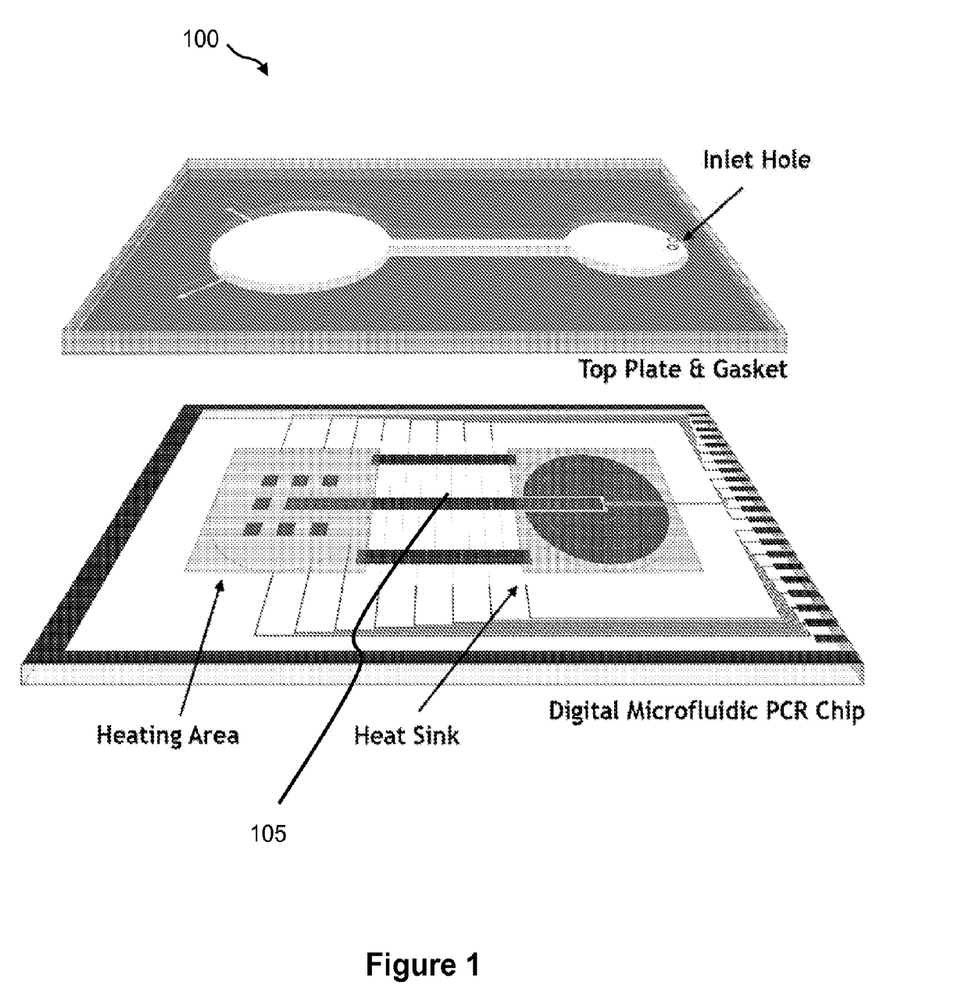

FIG. 1 illustrates a perspective view of a PCR chip assembly 100, which includes a digital microfluidic PCR chip and top plate. The invention provides a PCR droplet actuator that has a thermal gradient that is generated across the surface of the electrode array, which allows thermal cycling to be performed by transporting individual droplets between different positions within the thermal gradient.

PCR chip assembly 100 may be used to perform flow-through real-time PCR in microfluidic droplets by shuttling droplets along electrode path 105 along the temperature gradient to locations within the gradient suitable for conducting various steps in the amplification process, such as annealing, extension, and denaturation. Because the flow is programmable, thermal programs may be highly flexible, while the rapidity of droplet transport allows rapid cycling of temperatures. In one example, 40 cycles of real-time PCR is performed in less than about 5, 4, 3, or 2 minutes.

Referring again to FIG. 1, microfluidic devices, such as PCR chip assembly 100, may be fabricated by patterning chrome electrodes on glass slides using standard photolithographic techniques. A spacer/gasket (e.g., plastic) may be sandwiched between the patterned plate and a second glass containing an indium-tin-oxide (ITO) ground electrode. In one example, the electrode array may consist of a single linear array of 20 square electrodes at about 1.5 mm pitch. The unit droplet volume may, for example, be about ~100,000, 10,000, 2000, 1500, 1000 or 500 nL or less or volumes intermediate to such volumes, and other parameters of the droplet actuator, such electrode size, pitch and gap height may be adjusted accordingly.

Figure 2:
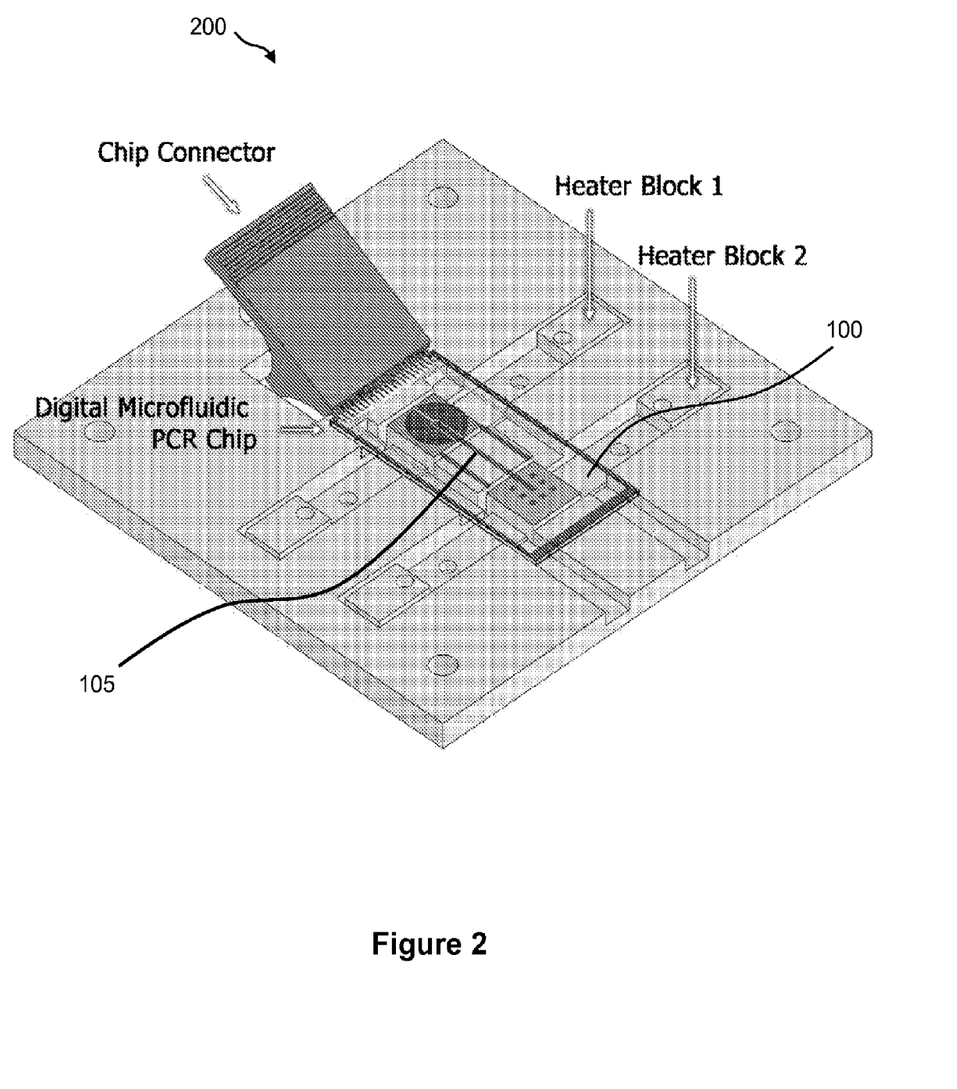

FIG. 2 illustrates a perspective view of a custom-made chip connector/heater assembly 200, which is an example mechanism for providing thermal control to, for example, PCR chip assembly 100 of FIG. 1. In one example, chip connector/heater assembly 200 includes an aluminum plate that contains two separate heater blocks each contacting a different area of PCR chip assembly 100 and each connected to independently controlled Peltier thermoelectric devices. A thermistor embedded in each block may be used for PID temperature control of the block. The internal temperature gradient of the chip may be calibrated with respect to the heater block and spatially mapped using both miniature thermocouples and melting point analysis of pure organic compounds.

Referring again to FIGS. 1 and 2, real-time fluorescence detection may be performed using a conventional fluorescence microscope, e.g., using a SYBR Green reaction. During the fluorescence detection operation, chip connector/heater assembly 200 may be mounted on the microscope stage and the fluorescence inside the droplet may be quantified using a sensitive photomultiplier tube (PMT). As an example, the PCR model assay was used to amplify a 273 bp fragment of *Candida albicans* 18S ribosomal RNA gene. The final reagent concentrations in the PCR reaction were be about 50 mM KCl, about 20 mM Tris-HCl pH 8.4, about 200 μM each dNTPs, about 25 U/mL iTaq polymerase, about 3 mM MgCl2, and about 0.2 M oligonucleotide primers.

Figure 3:
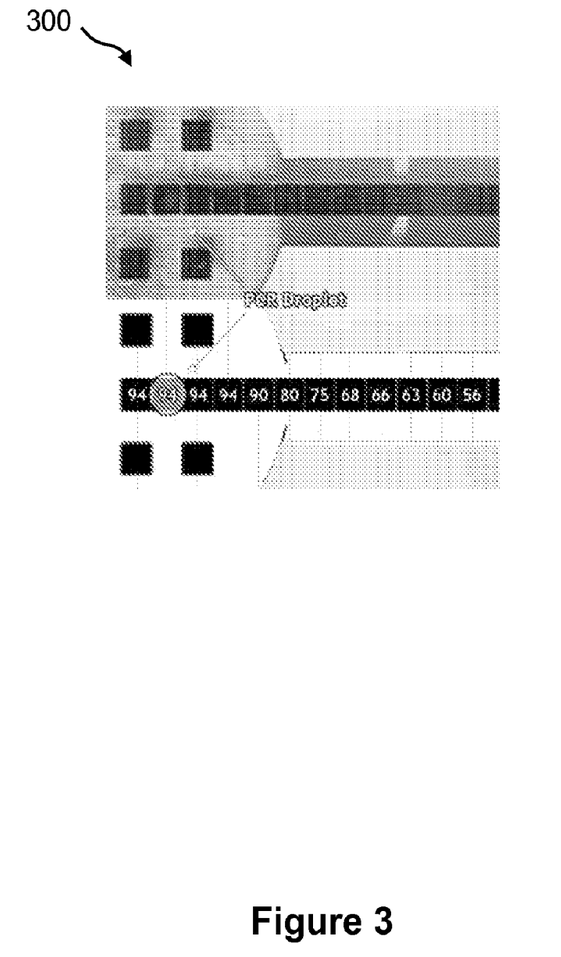

FIG. 3 illustrates a top view of an electrode array 300 that shows the relative location and position of the Peltier heater and PCR droplet (top) and thermal map of the electrode array (bottom). On-chip PCR experiments may be performed, for example, by manually pipetting or otherwise loading a 1000 mL reaction droplet into a chip that is filled with hexadecane in order to prevent evaporation. The droplet may then be cyclically transported between the 94° C. and 60° C. positions according to a user program. Additionally, the apparatus may be mounted on a fluorescence microscope that is focused on an electrode in the "extension" region to allow fluorescence measurement at the end of each cycle.

Figure 4:
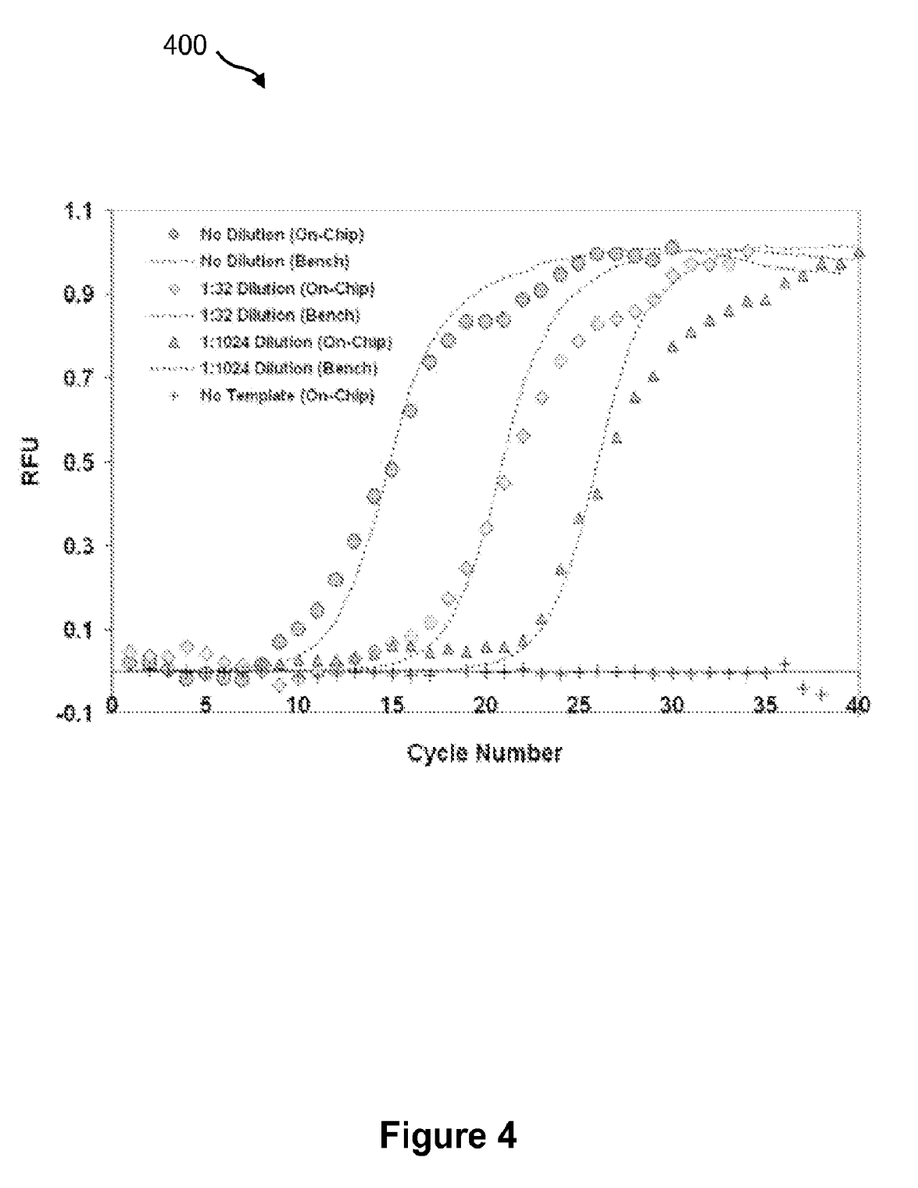

FIG. 4 illustrates a plot 400 of a comparison of an example of real-time PCR results for the chip-based system of the invention and a commercial benchtop thermocycler (e.g., BioRad iQ5) for varying concentrations of starting DNA. The results may be validated by agarose gel electrophoresis of the droplets that are collected at the end of each real-time experiment.

The time required for the sample droplet to transit between any two electrode positions of, for example, electrode array 300 of FIG. 3 is less than about 1 second, which allows much faster thermal programs to be performed on-chip than can be performed on the commercial system. An optimization may be performed using the chip system in which both the denaturation and annealing/extension times may be systematically reduced in order to determine the minimum analysis time. A different primer set that produces an 80-bp amplicon of the same gene may be used in these experiments, but the primer length remains substantially constant so that specificity is not lost in the transition.

Figure 5A:
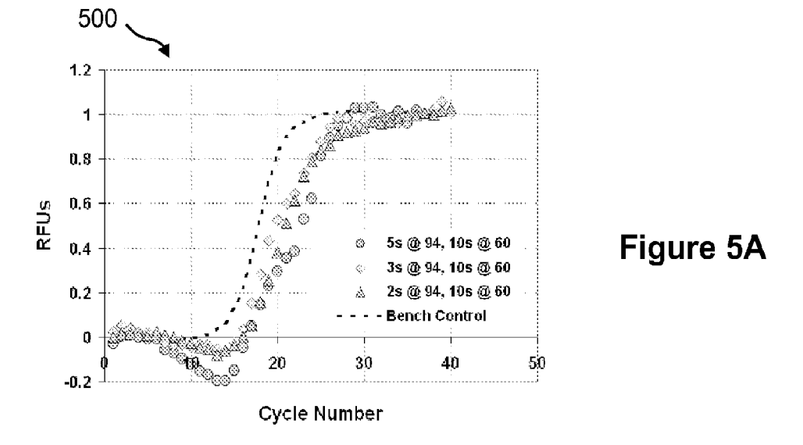
Figure 5B:
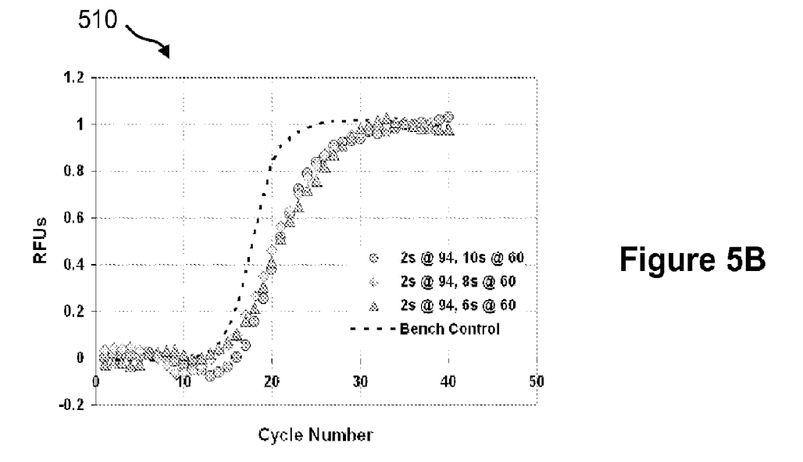
Figure 5C:
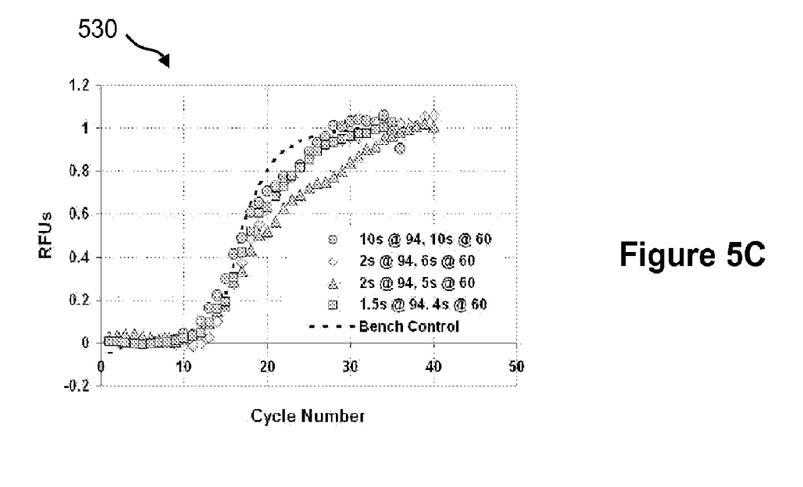

FIGS. 5A, 5B, and 5C illustrate a plot 500, a plot 510, and a plot 520, respectively, which shows a progression of speed optimization operations. Plots 500, 510, and 520 show real-time curves for optimization of time held at both the denaturing and annealing/extension temperature. The target amplicon was about 80-bp in length, allowing for a shorter extension period compared to the 273-bp amplicon. The results indicate that the fastest successful condition for amplification of the 80-bp target from a genomic template was 1.5 s @ 94° C. and 4 s @ 60° C. Combined with 2 s total transport time, this results in 7.5 s per cycle with 40 cycles of PCR performed in 5 minutes.

Aspects of performing rapid, programmable, real-time PCR using digital microfluidics include, but are not limited to (1) rapid thermal cycling—due to the low thermal mass and speed at which droplets can be transported; (2) precise control—programmably position droplets anywhere within a gradient; (3) flexibility—modify or change thermal programs in real-time through software; (4) scalability—multiple samples can be processed in parallel (with independent thermal programs if required); (5) integration—PCR can be integrated with other microfluidic operations (i.e. sample prep) on a single platform, (6) energy efficiency—heaters are not cycled and electrowetting consumes very little power, which is ideal for portable applications; and (7) multiplexed detection—multiple droplets can be scheduled for detection at a single fixed detection spot.

5.1 Droplet Microactuator

For examples of droplet microactuator architectures and PCR reagents and protocols that are suitable for use with the present invention, see U.S. Pat. No. 6,911,132, entitled, "Apparatus for Manipulating Droplets by Electrowetting-Based Techniques," issued on Jun. 28, 2005 to Pamula et al.; U.S. patent application Ser. No. 11/343,284, entitled, "Apparatuses and Methods for Manipulating Droplets on a Printed Circuit Board," filed on filed on Jan. 30, 2006; U.S. Pat. No. 6,773,566, entitled, "Electrostatic Actuators for Microfluidics and Methods for Using Same," issued on Aug. 10, 2004 and U.S. Pat. No. 6,565,727, entitled, "Actuators for Microfluidics Without Moving Parts," issued on Jan. 24, 2000, both to Shenderov et al.; Pollack et al., International Patent Application No. PCT/US 06/47486, entitled, "Droplet-Based Biochemistry," filed on Dec. 11, 2006, the disclosures of which are incorporated herein by reference. The term "chip" is used herein to refer to a "droplet actuator" chip.

5.2 Fluids

For examples of fluids that may be subjected to droplet operations using the approach of the invention, see the patents listed in section 5.1, especially International Patent Application No. PCT/US 06/47486, entitled, "Droplet-Based Biochemistry," filed on Dec. 11, 2006. In some embodiments, the fluid that is loaded includes a biological sample, such as whole blood, lymphatic fluid, serum, plasma, sweat, tear, saliva, sputum, cerebrospinal fluid, amniotic fluid, seminal fluid, vaginal excretion, serous fluid, synovial fluid, pericardial fluid, peritoneal fluid, pleural fluid, transudates, exudates, cystic fluid, bile, urine, gastric fluid, intestinal fluid, fecal samples, fluidized tissues, fluidized organisms, biological swabs and biological washes. In some embodiment, the fluid that is loaded includes a reagent, such as water, deionized water, saline solutions, acidic solutions, basic solutions, detergent solutions and/or buffers. In some embodiments, the fluid that is loaded includes a reagent, such as a reagent for a biochemical protocol, such as a nucleic acid amplification protocol, an affinity-based assay protocol, a sequencing protocol, and/or a protocol for analyses of biological fluids.

5.3 Filler Fluids

The gap is typically filled with a filler fluid. The filler fluid may, for example, be a low-viscosity oil, such as silicone oil. Other examples of filler fluids are provided in International Patent Application No. PCT/US 06/47486, entitled, "Droplet-Based Biochemistry," filed on Dec. 11, 2006.

We claim:

1. A method of amplifying a nucleic acid, the method comprising:
    (a) providing an amplification-ready droplet loaded operations gap of a droplet actuator, wherein the droplet actuator comprises:
        (i) two substrates separated to provide the droplet operations gap therebetween;
        (ii) electrodes associated with the substrates and arranged for transporting droplets in the droplet operations gap by electrowetting, the electrodes including an electrode path comprising electrodes arranged to transport droplets along the electrode path; and
        (iii) an oil-based filler fluid in the droplet operations gap at least partially surrounding the amplification-ready droplet;
    (b) applying heat to the droplet actuator to establish a temperature gradient of gradually varying temperature in the droplet operations gap, wherein the temperature gradient is established using a heating element arranged to heat filler fluid at a locus of the electrode path; and
    (c) cycling the amplification-ready droplet by using the electrodes to transport the amplification-ready droplet through the temperature gradient to locations within the temperature gradient having temperatures suitable for effecting steps in an amplification reaction, wherein the droplet is shuttled along the electrode path to different locations within the temperature gradient, and improved amplification patterns based on the results of varying the locations are identified.

2. The method of claim 1 wherein the droplet is shuttled through the oil-based filler fluid along the electrode path to the locations by using the electrodes to conduct electrowetting-mediated droplet operations on the droplet.

3. The method of claim 1 wherein the locations comprise locations having temperatures suitable for:
    (a) adjusting the droplet to a temperature selected to denature double stranded nucleic acid in the droplet into single-stranded DNA;
    (b) adjusting the droplet temperature selected to permit primers to anneal to their complementary sequences on the nucleic acid template strands; and
    (c) adjusting the droplet temperature selected to facilitate extension of the double stranded segment of the nucleic acid to be extended by incorporation of additional nucleotides.

4. The method of claim 1 comprising independently varying anneal location to identify an improved anneal location or temperature.

5. The method of claim 1 comprising independently varying extension location to identify an improved extension location or temperature.

6. The method of claim 1 comprising independently varying denaturation location to identify an improved denaturation location or temperature.

7. The method of claim 1 further comprising executing an improved PCR amplification protocol using the newly identified locations.

8. The method of claim 1 further comprising minimizing denaturation and annealing/extension times to reduce analysis time.

9. The method of claim 1 wherein the temperature gradient is established comprising:
    (a) using a heating element arranged to heat filler fluid at a first locus of the electrode path; and (b) a heat sink element arranged to heat filler fluid at a second locus of the electrode path.

10. The method of claim 1 further comprising mapping the temperature gradient.

11. The method of claim 1 further comprising mapping the temperature gradient to specific electrodes of the electrode path.

* * * * *